United States Patent [19]
Arnold et al.

[11] Patent Number: 5,452,069
[45] Date of Patent: Sep. 19, 1995

[54] SPARK SAMPLING MICROPARTICLE GENERATOR AND METHOD

[75] Inventors: James T. Arnold, Sunnyvale; Andrew T. Zander, Cupertino; Elbert S. Lile, Portola Valley; Charles B. Cooper, III, Redwood City, all of Calif.

[73] Assignee: Varian Associates, Inc., Palo Alto, Calif.

[21] Appl. No.: 137,854

[22] Filed: Oct. 15, 1993

[51] Int. Cl.⁶ ................... G01N 1/00; G01N 21/62
[52] U.S. Cl. ................................. 356/36; 356/316
[58] Field of Search .................... 356/36, 313, 316; 315/227 R, 209 CD, 209 M, 205

[56] References Cited

U.S. PATENT DOCUMENTS

| | | | |
|---|---|---|---|
| 2,758,238 | 8/1956 | Todd | 356/313 |
| 3,188,180 | 6/1965 | Höller | 356/313 |
| 3,791,743 | 2/1974 | Cody et al. | 356/36 |
| 3,942,892 | 3/1976 | Ambrose et al. | 356/313 |

OTHER PUBLICATIONS

Sainz et al. *Applied Spectroscopy*, vol. 43, No. 3, 1989 pp. 553–558.

Primary Examiner—F. L. Evans
Attorney, Agent, or Firm—Gerald M. Fisher

[57] ABSTRACT

A spark sampling microparticle generator device and method providing means to first ionize a gap and then to switch a stabilized and controllable current into and out of said ionized gap to provide extremely high, selectable current density in a sample material in said gap with very fast rise and fall times to ablate said material to form microparticles. A plurality of identical modular circuits containing high frequency power transistors are selectably switchably connected in parallel simultaneously to the gap to achieve current densities which are higher than achievable with a single transistor, thereby obtaining the benefits of the high frequency response without being limited by the current limitations of the available transistors.

13 Claims, 7 Drawing Sheets

SPARK SAMPLING MICROPARTICLE GENERATOR AND METHOD

FIELD OF THE INVENTION

Spark sampling method and apparatus for causing electric current to rapidly discharge into a solid sample, so as to create an aerosol containing small particles of the solid material to be analyzed and for providing such particles to remote spectroscopic analysis apparatus.

BACKGROUND OF THE INVENTION

Atomic spectrochemical analysis has been routinely carried out by determining the appropriate solvent, dissolving the sample to be analyzed and injecting the solution into an atomizer using a nebulizer to form an aerosol containing the sample. The aerosol particles are then treated to give spectroscopic indication of the atomic constituents present. The procedure of dissolving can produce background interference unless appropriate solvents and procedures are used. Accordingly, sample preparation has been generally a time consuming and tedious task. Also, many materials are not amenable to conversion to a stable solution, e.g. oxides, carbides, nitrides, and others. It has been appreciated in the prior art that it would be beneficial, more convenient and less expensive to provide an apparatus and methods for introducing solid samples directly into spectrometers without the dissolving step. One technique that has been employed is to use electrical discharge for the production of aerosols containing particles from conducting and nonconducting materials. Versions of this technique employ a high voltage spark and involve control of the spark voltage and current waveforms.

Sparks having short pulse widths, high repetition rate and high energy are known to produce finer particles and provide more reproducible sampling. It has also been known to employ very high voltage, short duration pulses to ionize an air gap between a sample and an electrode and then to provide one or more controlled current-waveform pulses of adequate duration to produce particles to make the aerosol. One paper reporting such an approach is Mohamed, et al., *Direct Sample Introduction of Solid Material into a Pulse Operation MIP*, Appl. Spectrsc., Vol 43, No. 5, pp. 793 (1989).

The current methods and apparatus for producing particles directly from a solid sample by spark ablation are not able to provide the same precision and accuracy as the older more ti me consuming dissolution/nebulization techniques. Accordingly, there is a need for more efficient and less costly but improved methods and apparatus for direct solid sampling.

SUMMARY OF THE INVENTION

It is an object of this invention to provide an improved spark discharge method and apparatus for creating sample microparticles from a solid sample.

A further object is to provide apparatus with electrical circuitry for improved shape and control of the current to the spark in order to bring about ablation of the solid material into reproducible particles sizes by using high frequency power transistors as switching elements.

An additional feature of the electrical circuit is that it provides very stable, adjustable repetition frequency, controllable high values of current at a high enough energy level to ensure ablation of the solid material into microparticles which are carried from the ablation crater site by an inert gas flow during the current pulse.

A still further feature is that the microparticle generator is less hazardous for the users because the circuit employs repeated charging and discharging of a capacitor where the capacitor is only charged with sufficient energy for one discharge.

A still further important feature is that high speed transistor devices are used in the current control circuitry in a modular configuration so that the total spark current can be increased as needed, selectively, by switching in additional modules in parallel, each of which provides an independently controlled portion of the total without overstressing the transistors in the individual modules.

DETAILED DESCRIPTION OF THE INVENTION

Figure 1:
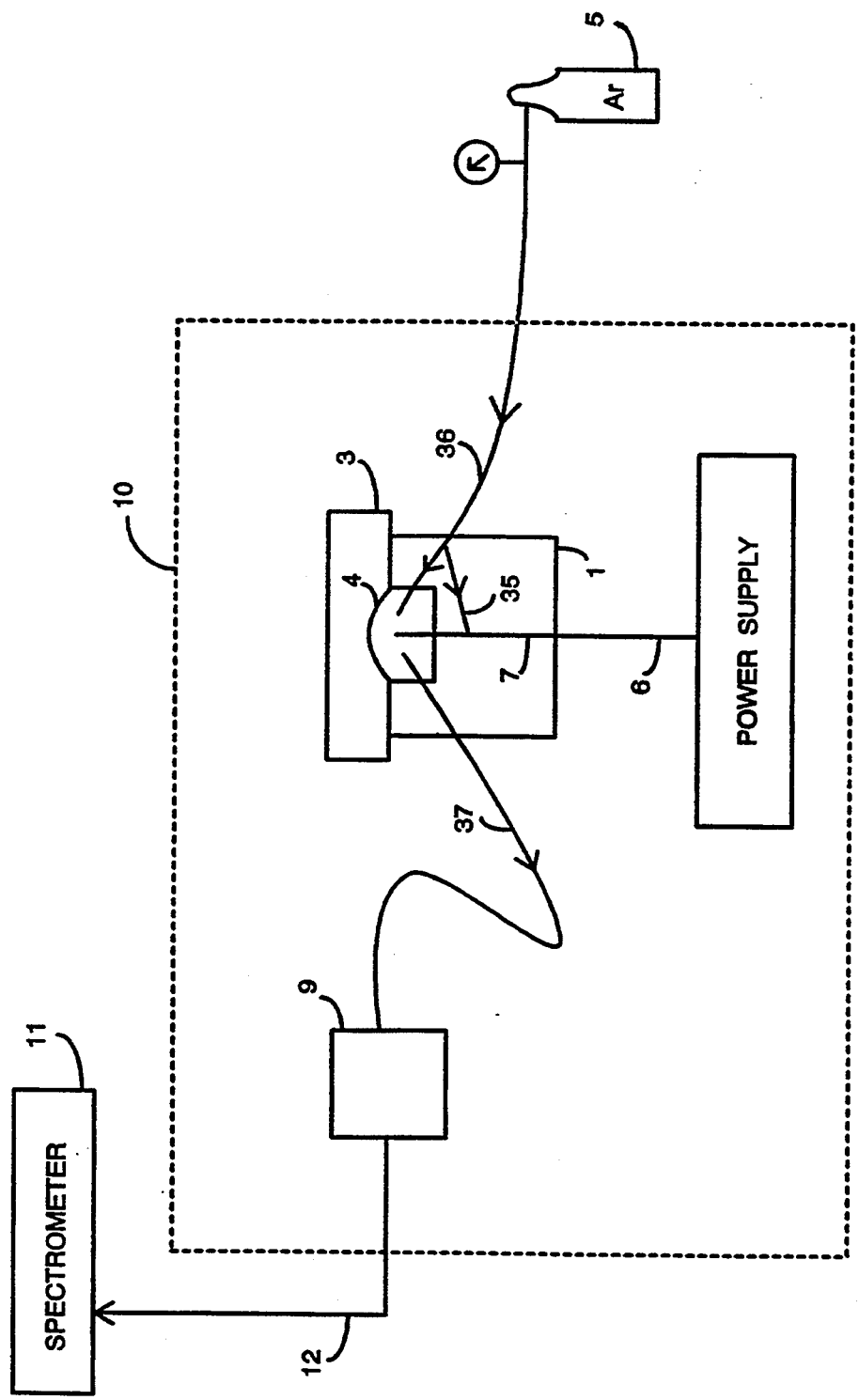
FIG. 1 is a block diagram of the interconnection of a spectrometer system and the instant microparticle generator invention.

The spark sampling microparticle generator 10 is schematically illustrated in FIG. 1. Microparticles generated are conveyed to an energetic means such as an inductively coupled plasma, I.C.P., to dissociate the particle into atoms and to excite those atoms for spectroscopic analysis as in a spectrometer 11 via a tubing 12. In operation, the tubing 12 supports a flow of a gas having micro size particles of a solid sample material 3 ablated from the sample mass entrained therewith. The sample particles are ablated by electrical pulses delivering concentrated energy to the sample surface within the sample chamber 23 of the microparticle generator. The gas is preferably an inert gas, such as argon, which is used to sweep the ablated microparticles from the spark gap 63 to the energetic means to dissociate the particles into atoms and to excite the atoms spectroscopically as in an inductively coupled plasma spectrometer (I.C.P.). Optionally, a settling tank 9 (or sizing filter) can be employed in the path to the spectrometer to remove those particles which are too large to be processed for example in the I.C.P. at the same time that the particles produced of nominal size are being analyzed. It is known that large particles may not become atomizer in an I.C.P. and can interfere with sustaining the plasma.

Figure 2:
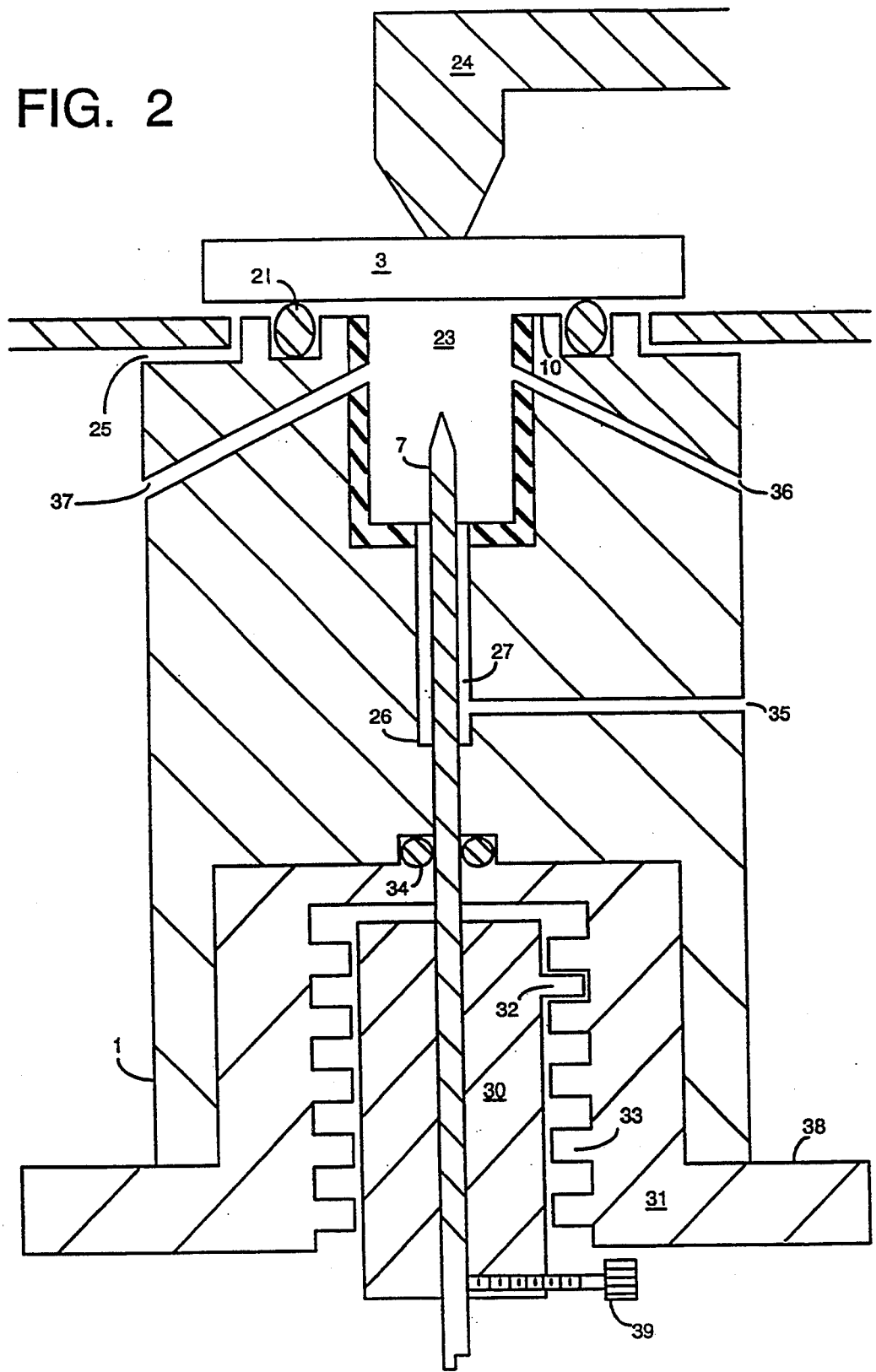
FIG. 2 is a cross section of the microparticle generator spark cell.

The preferred apparatus for physically applying the spark current to the sample is shown in FIG. 2. The sample 3, preferably in the flat disk form, is clamped to the upper surface of the sample chamber assembly 1 annular ring 10 by clamp 24 against O-ring 21 to maintain a fluid sealed tight cavity 23 between the sample and the body of the sample chamber assembly 1 (except for ducts 35, 36 and 37). An electrode of refractory metal, such as tungsten 7, having a sharpened tip with means to adjust the length of the gap between the sample and the electrode tip in the chamber 23. The sample chamber assembly 1 is made of electrically non-conductive material and has several ducts 35, 36 and 37 therein for a sweeping gas flow to carry the microparticles from the cavity to the spectrometer and for assisting in maintaining the spark.

The tungsten rod electrode 7 is captured by set screw 39 in a metal cylinder 30 which can slide but not rotate within the internally threaded insulated bushing 31. The metal cylinder is fitted with bosses 32 which engage the threads 33 of the bushing 31 so that the cylinder 20 and the captive electrode 7 can be moved axially to adjust the gap distance 63 by rotation of the bushing 31. This arrangement of bushing, gear teeth and rotation constrained cylinder comprises a rotary motion to linear motion converter. The annular space 27 is isolated and sealed to the chamber 23 by O-ring 34, and gas is introduced through port 35 and 36 to assist in the gas sweeping through the chamber. The clamp 24 is grounded in operation and contacts the sample body 3, making the sample body the counter electrode to the rod 7.

We have found that spark pulses of uniform current with very steep onset and cut off provide the most consistent analytical results. It is postulated that the high current density, as the current flows into sample surface, creates extremely large local deposit of energy which results in displacement of microparticles from the surface of the sample material. It has been shown that it is necessary to first provide initiating ions in the gas in the gap before the high current spark can be initiated. We have found that for best results, the current in the spark should rise steeply and be regulated. Our preferred method includes a solid state switch bypassing the gap 63 which switch is initially closed to allow the current regulator to stabilize, and is then opened to permit the regulated current to build up very rapidly in the gap while the initiating ions remain in the gap. This method provides a low cost means to switch high currents rapidly into the gap. Earlier techniques of current regulation during rapidly changing current levels have proven to be very difficult and expensive.

Figure 3A:
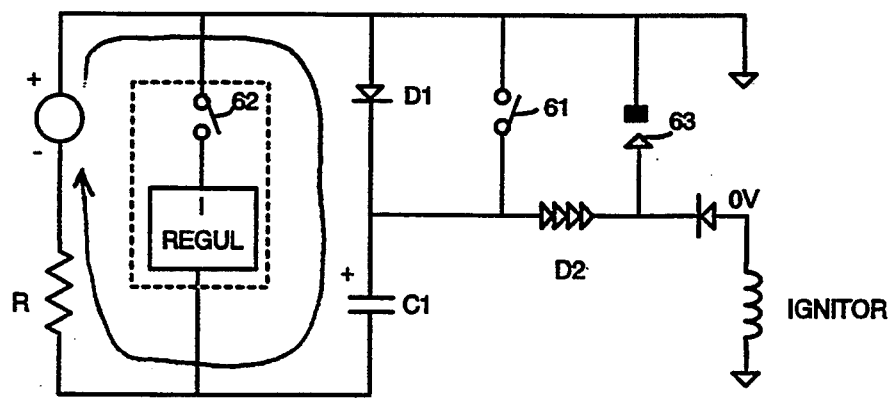
FIG. 3A, 3B and 3C are schematic electrical diagrams which illustrate the current switching of the instant invention.

With reference to FIG. 3A, and for a relatively long period approximately one millisecond, the capacitor C1 is charged from the 160 v power supply through diode D1 and resistor R. During this initial period, switch 61 and 62 are open and the ignitor is off so no current flows in the gap 63.

Figure 3B:
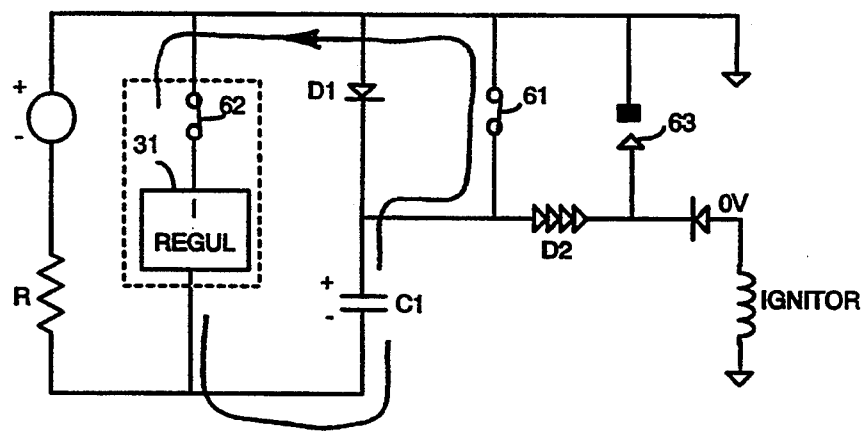
Figure 3C:
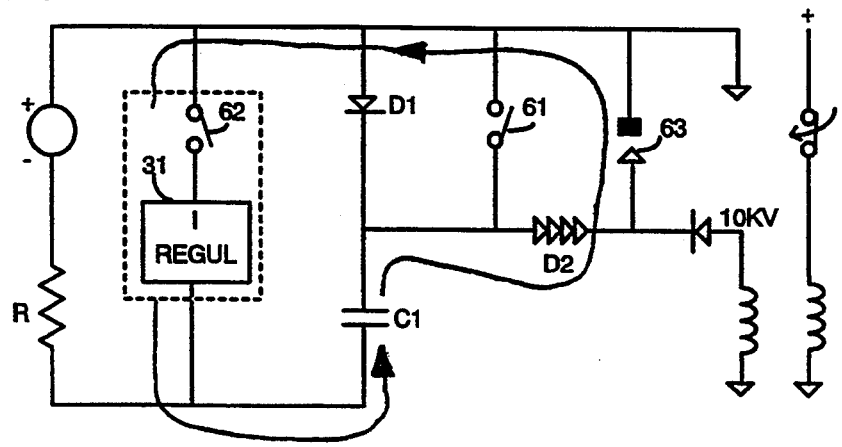

In the next time interval, the current regulator is activated and the current switch 62 and spark gap switch 61 are closed. As shown in FIG. 3B, the capacitor C is now the principal source of current for the circuit and the regulator establishes a regulated high current value, e.g., 20 amps, in the circuit. Since gap 63 is not in electric breakdown and switch 61 shunts the gap 63, none of the current flows through diodes D2 into gap 63 during this period.

In the next period, the ignitor is fired and a very high voltage, for example, up to 10 KV is applied across the gap 63. This high voltage initiates ionization of the gas in the gap and dramatically reduces the gap impedance. Shortly after the ignitor fires, in the range of 1 microsecond, the spark switch 61 opens and the regulated current which had been previously flowing through switch 61 is diverted into gap 63 through the high speed diodes D2.

Figure 4B:
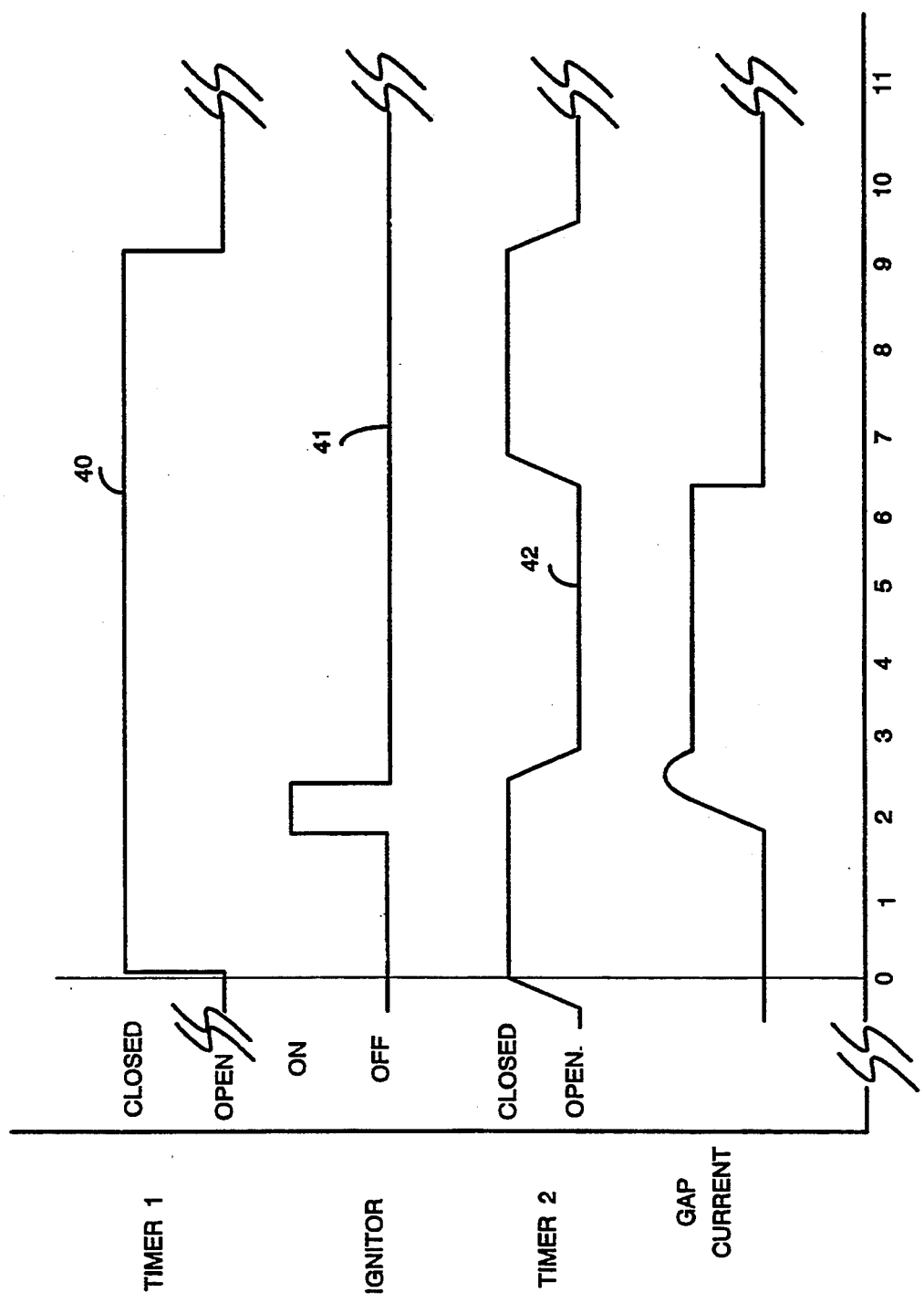
FIG. 4B is a timing diagram showing typical control waveforms and their timing interrelationships.
Figure 4A:
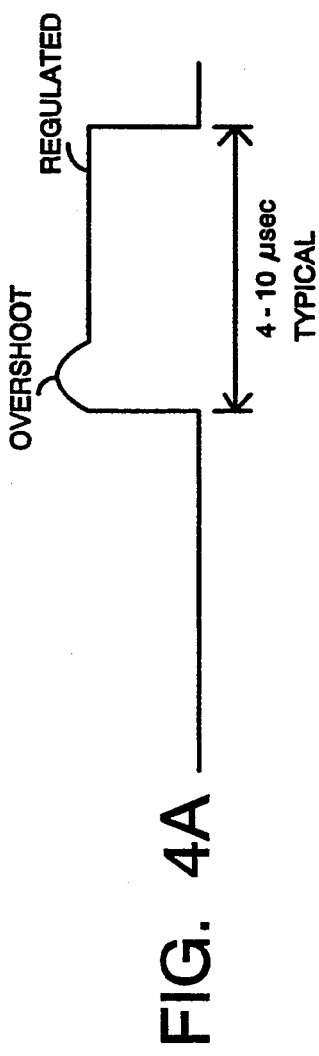
FIG. 4A is a drawing of the time dependence current in the spark gap as provided by the invention.

By switching at very high rates, as is possible with high frequency MOSFET transistor power switches, we have been able to provide very clean rapidly rising and falling gap current pulses of adjustable pulse length having the shape illustrated in FIG. 4A.

Figure 4C:
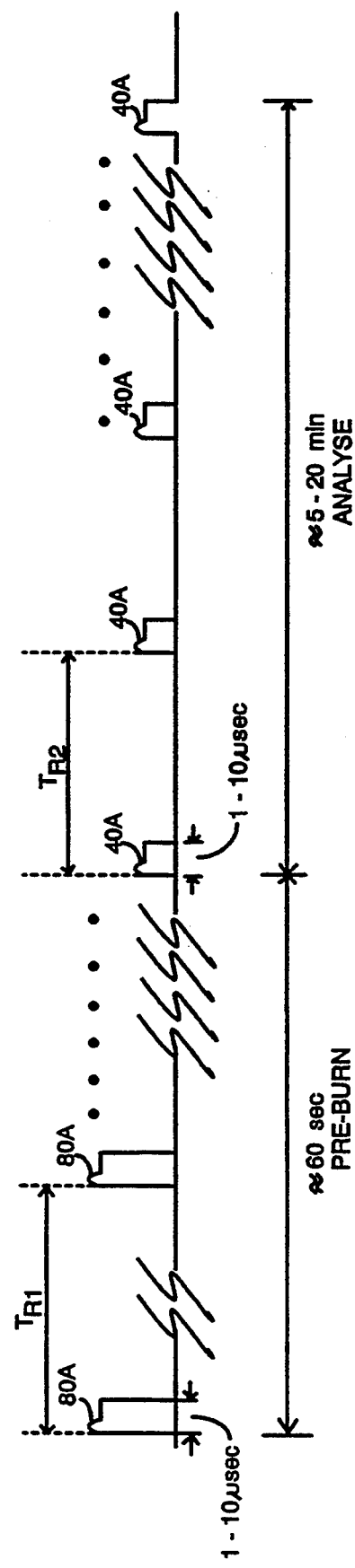
FIG. 4C is a timing diagram illustrative of typical burn-in and analyze gap currents for an entire experiment.

With reference to FIG. 4C, the width of these individual short current pulses are illustrated in relationship to the microparticle generator sequences. Generally, an experiment is initiated by a burn-in period, which is of selectable time but is usually around 60 seconds. We have found that this preburn procedure produces more reliable analyses. During the preburn period, the current pulse is normally selected at a higher level such as 80 amps and the pulse repetitious period $T_{RI}$ is also selectable but is usually approximately 1 millisecond. Following the burn-in period, the analysis period commences during which time the current level is normally selected to be lower. We have found that lower level pulses delivered at lower rates give better spectroscopic results. The pulse length, repetition period, and the length of analysis time are all selectable for any experiment. As can be seen, the duty cycle is low, on the order of 1/100, which provides more than enough time between pulses to charge the capacitor with the energy required in the pulse that follows. The relatively small total charge stored tends to provide the safety advantage of not requiring very high energy storage.

It is noted that in order to provide the desired high speed switching that MOSFET high power transistors called IRF640 available from International Rectifier Corporation and others, have been employed. These transistors are not capable of providing the full 80 ampere high current to the spark as required for this application, even at the low duty cycle. Accordingly we have provided a modular design in which each unit is capable of providing a separately regulated current of 20 amperes. In the preferred embodiment, we provide four modules which can be selectively connected in parallel to provide 80 amperes for the burn-in period.

Figure 5A:
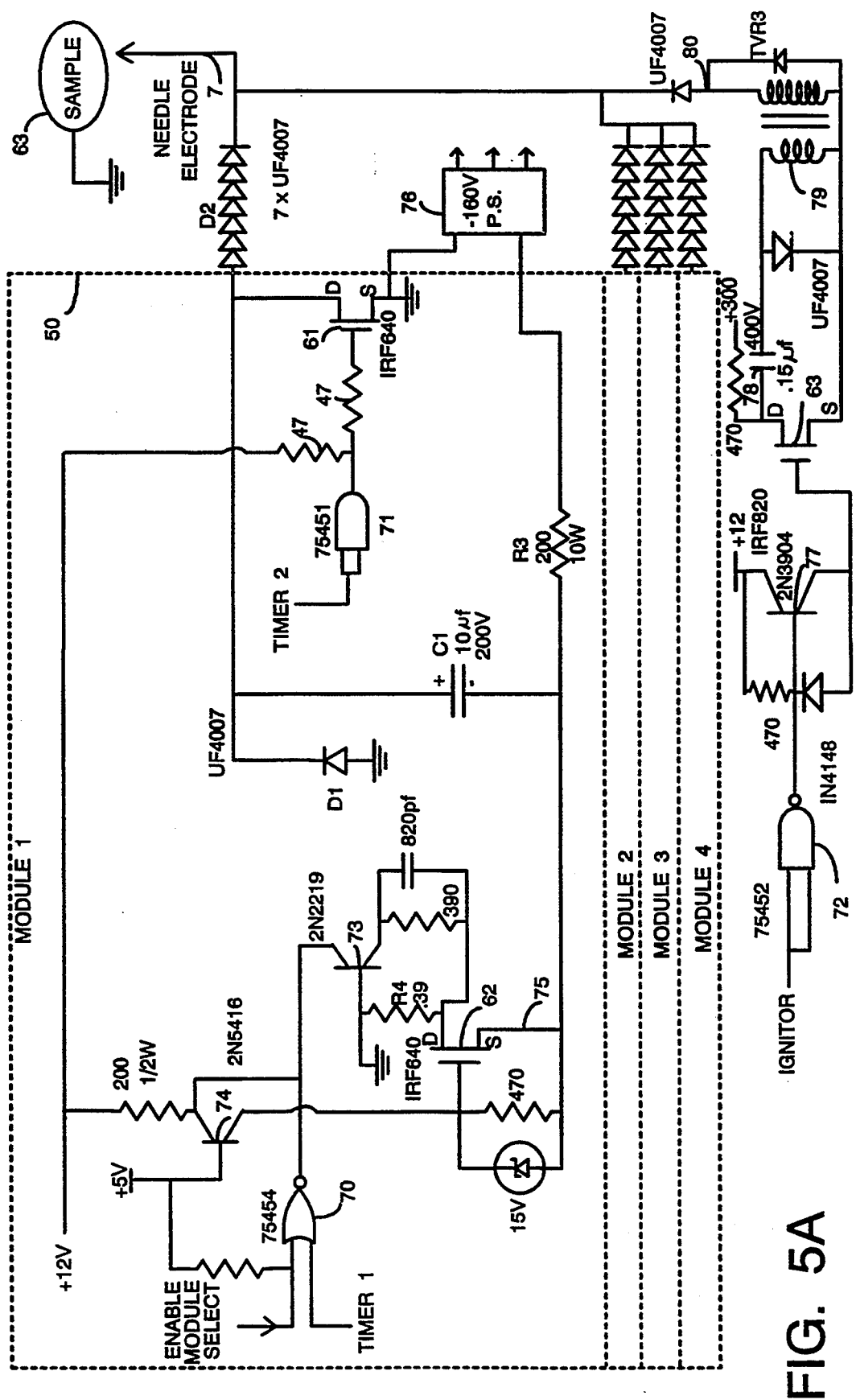
FIG. 5A is an electrical schematic diagram of the preferred embodiment of the current generator and switch for the microparticle generator.

With reference to FIG. 5A, we show schematically the detailed preferred embodiment of one of the modules of the regulated pulse power controller. In module 1 (50) as described earlier, power transistors 61 and 62 control the switching of a regulated current into the gap 63. Modules 51, 52 and 53 are identical to module 50 which is shown in detail.

Transistor 61 is connected to the positive terminal of power supply 76 which is also connected to ground. The negative terminal of the power supply is connected to a current limiting 200 $\Omega$, 10 W charging resistor R3, the other side of which is connected to 10 $\mu f$, 200 V capacitor able to provide high current surges. This node is also connected to the source of the high current switch MOSFET transistor 62. Across the transistor 62 gate to source is a parallel network of a 470 $\Omega$ and protective 15 V zener diode. Connected between the drain of the transistor 62 and ground is a 0.39 $\Omega$ reference resistor which is connected via a resistor/capacitor network to the emitter of transistor 73. The signal developed in the 0.39 ohm reference resistor is representative of the current delivered, and becomes the control error signal for the servo amplifier formed by the gain of transistors 73 and 74. The collector of transistor 73 is connected to the emitter of transistor 74. The base of transistor 74 is connected to +5 V and the emitter of transistor 74 is coupled to +12 V through a 200 Ω resistor. Also connected to the emitter of the regulator transistor 74 is the output of the inverted OR gate 70. The OR gate 70 switches the regulator and the current switch 62 on/off by selectively diverting current from the 200 ohm resistor.

The drain of the other power transistor 61 is connected to a common node between D1 diode and the string of 7 diodes (D2). D2 is to protect the circuit from the high ignitor voltage. The diode D1 is poled to support the capacitor charging from power supply 76 as explained in connection with FIG. 3A. Connected to the gate of the transistor 61 is the timing control timer 1 through AND gate 71 via a 47 Ω resistor. The 12 V supply also connects to the output of the AND gate 71 via a resistor to furnish fast rise time pulses.

Amplifier transistor 73 and transistor 74 in conjunction with power transistor 62, provide the current regulator. The current which flows through transistor 62 also flows through reference resistor R4. If the current is greater than 20 amps, current drawn in transistor 73 is increased, thereby reducing the voltage to the emitter of transistor 74. As this occurs, transistor 74 conducts less and reduces the bias from gate to source on the transistor 62 tending to reduce the current.

A single ignitor circuit provides a fast switching current through the primary of transformer 79 resulting in a 10 Kv pulse at the output 80 of the transformer secondary. This high voltage is connected to the sharpened electrode 7 to initiate ionization in the gap for all settings of current to the spark.

FIG. 4B depicts the timing diagram for the pulses for the control of the spark operation. After the capacitor has charged, during the off portion of the duty cycle, the pulse control circuits generate the sequences of FIG. 4B. Corresponding to FIG. 3B, the current regulator is turned on and the current regulator 62 is activated at about the same time that the switch 61 is closed. This step provides a regulated 20 amps into the circuit containing switch 61. Next, approximately 1.5 microseconds later, the ignitor pulse issues, and approximately 0.5 microseconds later, the switch 61 opens, and the prestabilized current is rapidly switched into the gap 63 via ultra fast diodes D2. After the lapse of a preselected time, typically 4–10 microseconds, the current in the gap is switched back into transistor 61 as it closes at that time. This cuts off the current pulse in the gap and thus determines the spark pulse width. After this, the current regulator 62 is switched off, whereupon the switch 61 can also be switched back to open. The gap current pulse is seen to be very clean, sharp and highly controllable with fast rise and fall using the methods and circuits of the invention.

Standard timing circuit are available to generate the transistor control pulses 40, 41 and 42 from FIG. 4B.

Figure 5B:
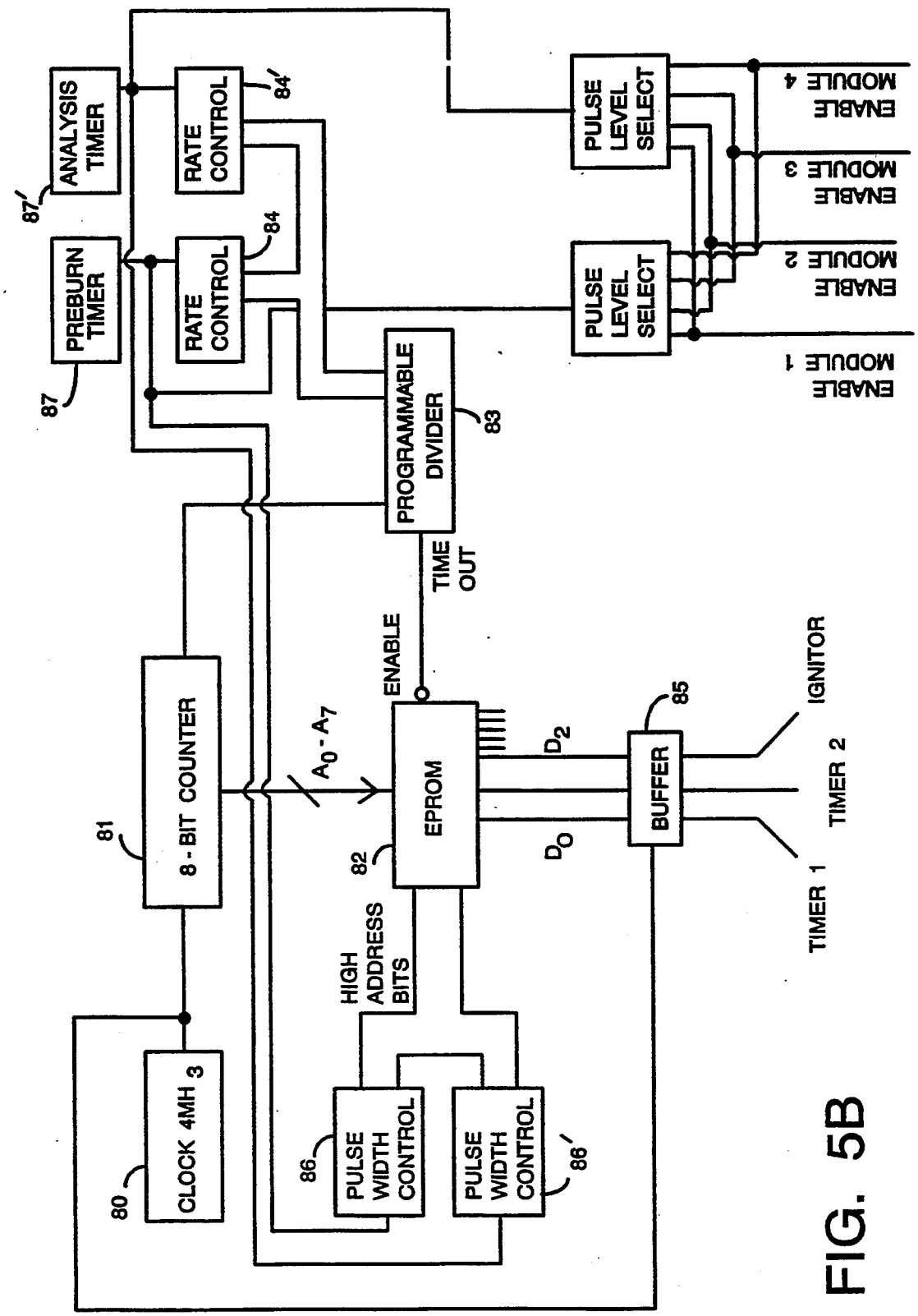
FIG. 5B is a block diagram of the compete electrical scheme used in the microparticle generator for timing control.

The timing circuit we employ uses an EPROM to store the timing profile for the selections made available. The EPROM is segmented by switch selecting of higher address bits. The higher addresses call up programmed pulse sequences according to operator switch selection. Using 16 bits of addressable memory and providing 8 bits for each segment provides the ability to select up to 256 programmed sequences. In our device, we use only a few of the available segments. With reference to FIG. 5B, we use a 4 MHz oscillator 80 and a series counter register 81 to generate an incrementing 8 bit output which is used to provide address bits for the EPROM. The user has available on the front panel of the micro particle generator 10 a selector 86 and 86' for preburn and analysis periods which enables certain pulse width selections. These selections are entered as high bit address bus lines and input to the EPROM 82. The user also has a selector 84 and 84' and 87 and 87' for selecting the repetition rates for preburn and analysis periods. Selecting the desired repetition rate controls a programmable divider. At the terminal count of this divider, a single output lasting for 256 clock pulses is delivered to the output enable of the EPROM to release a single spark sequence. The high address bits sent to the EPROM determine which segment is output on the EPROM data lines as the low address is incremented by the 4 MHz clock. For each selected high address, we use three simultaneous outputs from the EPROM on data lines $D_0$–$D_2$. The output voltage on each of the three data lines is a one bit binary signal which actuates the control line to which it is connected via the buffer 85. The action of the buffer is to furnish clean signals to the control lines.

Separate front panel switches of the microparticle generator 10 are provided to control the parameters of the preburn and analysis cycles. Selection is via two sets of diode matrices under control of two front panel timers furnished for the preburn and analysis cycles respectively. Each time period controlled by 87 and 87' can be preset by the operator, and when a operation is initiated, the sequence from the first timer to the second timer is automatically executed. It is not our intention to limit our invention to the specific embodiment of our drawings since there are other forms within our concepts to achieve our invention. Accordingly, the scope of our invention should be determined by our claims.

What is claimed is:

1. In a spark apparatus for ablating sample from a solid material to be analyzed to create microparticles from said material by use of high intensity electrical sparks and to move said microparticles to an analyzer including (a) means to mount said material to be sampled to said spark apparatus;
   (b) means to cause partial ionization in gas in the space between said spark apparatus and said sample;
   (c) means to control the electric current flowing in said ionized gas, THE IMPROVEMENT COMPRISING a module including;
   (d) means to establish a stabilized current value in a circuit external to said ionized space;
   (e) capacitor means to store sufficient energy in said external circuit for one spark pulse wherein said capacitor means charges during the period before said stabilized current is established in said external circuit;
   (f) said means to establish a stabilized current comprises means to obtain the energy for said current from said capacitor means;
   (g) means to switch said stabilized current from said external circuit to flow into said space containing gas ions, said means to switch for switching said stabilized current into said space containing ions causing further increase in ionization and permitting flow of high current; and (h) means to switch said stabilized current out of said space containing ions and back into said external circuit after a predetermined selectable interval.

2. The apparatus of claim 1 wherein said means to switch said stabilized current value in a circuit external to said ionized space comprises a pair of high speed power transistors wherein each said transistor has a permitted maximum current value and wherein said permitted maximum current value is not high enough to cause optimum ablation of said sample, and wherein said means to switch said stabilized current value includes means to provide enough current to cause ablation of said sample.

3. The apparatus of claim 2 wherein said means to provide enough current to ablate said sample includes means to connect in parallel additional modules containing additional pairs of said high speed power transistors.

4. The apparatus of claim 3 wherein each said module is identical and wherein a desired gap current is obtained by providing a plurality of said modules in parallel until said desired gap current is obtained without exceeding the maximum permitted current for any power transistor in any module.

5. The method for making microparticles of material to be analyzed in a spectrometer comprising:
(a) mounting said material to be analyzed in fluid sealing relationship in a spark apparatus, said spark apparatus having a cavity with a sharp pointed electrode therein, said cavity further containing a gas therein, said sharp pointed electrode being displaced from said material by a gap;
(b) establishing a stabilized current in each of a plurality of identical circuits external to said cavity;
(c) ionizing said gas in said gap of said cavity with a high voltage pulse applied to said electrode;
(d) switching said stabilized current into said gap as the high voltage pulse is ending but while said gap remains ionized by simultaneously switching the current from a selected number of said plurality of identical circuits into said gap; and
(e) switching said stabilized currents out of said gap and back into said plurality of identical circuits after a time period.

6. The method of claim 5 wherein said step of switching a predetermined amount of stabilized current pulses into said gap includes a first so called preburn period and a second so called analysis period and where a different number of said plurality of identical circuits are switched into circuit with said gap during said first and second periods and whereby more such circuits are switched into circuit with said gap during said first burn-in period.

7. The method of claim 5 wherein said stabilized current is switched into said gap for a small portion of each pulse period.

8. The method of claim 7 wherein said small portion is in the range 0.2% to 1%.

9. The method claim 6 wherein said stabilized current is switched into said gap for a small portion of each pulse period.

10. The method of claim 5 wherein a large value capacitor is charged in each said plurality of identical circuits prior to said step of establishing a stabilized current in said spark apparatus external to said gap; and wherein each said large value capacitor supplies said stabilized current into said gap from each said identical circuit during the period that said stabilized current from said plurality of identical circuits is switched into said gap.

11. A spark circuit for generating microparticles comprising:
(a) a sample compartment including a first pointed electrode, and a second electrode; said second electrode being made from a solid material to be analyzed, said first and second electrode being separated by a space containing a gas;
(b) an ignitor, said ignitor being connected to said first pointed electrode, for providing a high voltage short duration pulse sufficient to ionize said gas in said space between said first and second electrode;
(c) a first transistor power switch having a gate, drain and source;
(d) a capacitor, said capacitor having a first and second terminal;
(e) a string of series connected diodes connected to said first pointed electrode on one end of said string of diodes and to a first terminal of said capacitor and to said drain of said first transistor power switch on the opposite end of said string of diodes;
(f) a DC power supply having positive and negative terminals, said DC power supply being connected to a first terminal of a first current limiting resistor, said positive terminal of said DC power supply being connected to said source of said first transistor power switch and to said second electrode of said sample compartment, said first current limiting resistor having a second terminal; and
(g) a second transistor power switch having a source, drain and gate, said source of said second transistor power switch being connected to said second terminal of said first current limiting resistor and to said second terminal of said capacitor.

12. The apparatus of claim 11 wherein said drain of said second transistor power switch is connected to a reference resistor whereby said capacitor discharges through said space when said first transistor power switch becomes non-conducting and wherein the capacitor discharge circuit includes a path through said reference resistor and said second transistor power switch.

13. The apparatus of claim 12 including a pair of amplifier transistors for regulating the current in said second transistor power switch in response to the current through said reference resistor.

* * * * *